(12) United States Patent
Kim et al.

(10) Patent No.: US 9,719,905 B2
(45) Date of Patent: Aug. 1, 2017

(54) METHODS OF MEASURING ELECTRODE DENSITY AND ELECTRODE POROSITY

(71) Applicant: LG Chem, Ltd., Seoul (KR)

(72) Inventors: Eun Kyung Kim, Daejeon (KR); Sun Young Shin, Daejeon (KR); Je Young Kim, Daejeon (KR); Sang Wook Woo, Daejeon (KR)

(73) Assignee: LG Chem, Ltd. (KR)

( * ) Notice: Subject to any disclaimer, the term of this patent is extended or adjusted under 35 U.S.C. 154(b) by 538 days.

(21) Appl. No.: 14/331,510

(22) Filed: Jul. 15, 2014

(65) Prior Publication Data

US 2014/0336975 A1 Nov. 13, 2014

Related U.S. Application Data

(63) Continuation of application No. PCT/KR2014/003801, filed on Apr. 29, 2014.

(30) Foreign Application Priority Data

May 9, 2013 (KR) .................. 10-2013-0052345

(51) Int. Cl.
G01N 9/36 (2006.01)
G01N 23/207 (2006.01)
H01M 4/133 (2010.01)

(52) U.S. Cl.
CPC ............ *G01N 9/36* (2013.01); *G01N 23/207* (2013.01); *G01N 2223/633* (2013.01); *G01N 2223/649* (2013.01)

(58) Field of Classification Search
CPC ........ G01N 9/36; G01N 23/207; H01M 4/133
See application file for complete search history.

(56) References Cited

U.S. PATENT DOCUMENTS

| 2003/0052013 A1 | 3/2003 | Ando et al. | |
| 2004/0023115 A1* | 2/2004 | Kato | H01M 2/0285 429/231.8 |

(Continued)

FOREIGN PATENT DOCUMENTS

| CN | 1906780 A | 1/2007 |
| CN | 102484244 A | 5/2012 |

(Continued)

OTHER PUBLICATIONS

Suda, Souichirou et al., "Anode Material for High Energy Density Rechargeable Lithium-Ion Battery." American Carbon Society, Jul. 20, 2007, XP055258800, http://acs.omnibooksonline.com/data/2007.htm.

(Continued)

*Primary Examiner* — Bryan Bui
(74) *Attorney, Agent, or Firm* — Lerner, David, Littenberg, Krumholz & Mentlik, LLP

(57) ABSTRACT

Provided is a method for non-destructively measuring an electrode density and an electrode porosity of an electrode active material coated on an electrode base material using X-ray diffraction. According to the methods of the present invention, a value of $I_{peak\ in\ parallel\ direction}/I_{peak\ in\ perpendicular\ direction}$ of the electrode active material is obtained by X-ray diffraction and an electrode density and an electrode porosity are calculated according to previously obtained correlations between the electrode density and $I_{peak\ in\ parallel\ direction}/I_{peak\ in\ perpendicular\ direction}$ and between the electrode porosity and $I_{peak\ in\ parallel\ direction}/I_{peak\ in\ perpendicular\ direction}$.

10 Claims, 7 Drawing Sheets

(56) References Cited

U.S. PATENT DOCUMENTS

| | | |
|---|---|---|
| 2011/0045353 A1 | 2/2011 | Ishii et al. |
| 2012/0164530 A1 | 6/2012 | Temmyo et al. |
| 2012/0183839 A1 | 7/2012 | Yuasa et al. |
| 2013/0115508 A1 | 5/2013 | Hoshina et al. |
| 2015/0318545 A1* | 11/2015 | Satow .................. H01M 4/133 429/324 |

FOREIGN PATENT DOCUMENTS

| | | |
|---|---|---|
| CN | 103022416 A | 4/2013 |
| EP | 1720211 A1 | 11/2006 |
| EP | 1775789 A2 | 4/2007 |
| JP | 2001-351687 A | 12/2001 |
| JP | 2003-317708 A | 11/2003 |
| JP | 2010-267629 A | 11/2010 |
| JP | 2011-076820 A | 4/2011 |
| JP | 2012-094354 A | 5/2012 |
| JP | 2013069429 A | 4/2013 |
| KR | 2002-0029944 A | 4/2002 |
| KR | 20070041358 A | 4/2007 |
| KR | 2012-0106512 A | 9/2012 |

OTHER PUBLICATIONS

International Search Report from PCT/KR2014/003801, dated Aug. 14, 2014.
Yoshito Ishii, et al., "Anode Material for High Energy Density Rechargeable Lithium-ion Battery." Hitachi Chemical Technical Report, 2006, No. 47, p. 29-32 (English translation of Abstract only).

* cited by examiner (A)

(B)

(C)

(A)

(B)

METHODS OF MEASURING ELECTRODE DENSITY AND ELECTRODE POROSITY

CROSS-REFERENCE TO RELATED APPLICATIONS

The present application is a continuation of International Patent Application No. PCT/KR2014/003801, filed Apr. 29, 2014, which claims the priority from Korean Application No. 10-2013-0052345, filed May 9, 2013, in the Korean Intellectual Property Office, the disclosures of which are incorporated herein by reference.

TECHNICAL FIELD

The present invention relates to methods of measuring electrode density and electrode porosity using X-ray diffraction.

BACKGROUND ART

Recently, in line with miniaturization, lightweight, thin profile, and portable trends in electronic devices according to the development of information and telecommunications industry, the need for high energy density batteries used as power sources of such electronic devices has increased. Currently, research into lithium secondary batteries, as batteries that may best satisfy the above need, has actively conducted.

In general, an electrode density or electrode porosity of electrodes used in a lithium secondary battery is obtained in a state in which a slurry is prepared by mixing a cathode or anode active material with a solvent, if necessary, a binder and a conductive agent and stirring, an electrode base material of a cathode or anode formed of a metallic material is coated therewith and dried, and the dried electrode based material is then pressed at an appropriate pressure. In this case, the electrode density is increased while the porosity decreases as the applied pressure increases.

In the lithium secondary battery, the electrode density and electrode porosity may be related to various battery characteristics including energy density of the battery, electrical conductivity of the electrode, and ionic conductivity. Thus, appropriate electrode density and electrode porosity may be different from desired battery characteristics, and it is very important to minimize the deviation thereof in a production process of the electrode.

To date, a method of measuring an electrode density (D) is performed in such a manner that weight and thickness of an electrode are measured by sampling a specific area of the electrode when needed, and the density is measured using a value in which mass and thickness of an electrode base material, i.e., a metal such as copper or aluminum, having the same area are subtracted from the respective measured values.

Also, the electrode density obtained by sampling the specific area of the electrode is subtracted from 1 to obtain a value, and an electrode porosity (P) is obtained by dividing the value by the density of the electrode excluding the electrode base material and then calculating in terms of percentage.

The measurements of the electrode density and the electrode porosity by the above methods may have the following limitations. First, since an electrode must be sampled whenever density and porosity of each electrode are needed, a portion of the electrode must be destructed for each measurement. Thus, it may be time consuming as well as cost consuming. Also, since an electrode base material must be dissolved in a predetermined solvent to measure the density and thickness of the electrode excluding the electrode base material, a measurement process may be complicated.

Therefore, there is a need to provide a method of efficiently measuring electrode density and electrode porosity while not destructing an electrode to be measured and reducing errors.

DISCLOSURE OF THE INVENTION

Technical Problem

The present invention provides a method of efficiently measuring electrode density and porosity by a non-destructive method using X-ray diffraction.

Technical Solution

According to an aspect of the present invention, there is provided a method of measuring an electrode density including obtaining an $I_{peak\ in\ parallel\ direction}/I_{peak\ in\ perpendicular\ direction}$ value of an electrode active material, on which a density is to be measured, by X-ray diffraction; and calculating a targeted electrode density according to a correlation between the electrode density and the $I_{peak\ in\ parallel\ direction}/I_{peak\ in\ perpendicular\ direction}$ value of the electrode active material which are obtained in advance.

According to another aspect of the present invention, there is provided a method of measuring an electrode porosity including 1) obtaining an $I_{peak\ in\ parallel\ direction}/I_{peak\ in\ perpendicular}$ direction value of an electrode active material, on which a porosity is to be measured, by X-ray diffraction; and 2) calculating a targeted electrode porosity according to a correlation between the electrode porosity and the $I_{peak\ in\ parallel\ direction}/I_{peak\ in\ perpendicular\ direction}$ value of the electrode active material which are obtained in advance.

Advantageous Effects

According to methods of measuring electrode density and porosity of the present invention, electrode density and electrode porosity may be efficiently measured by a non-destructive method using X-ray diffraction.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

A method of measuring an electrode density according to an embodiment of the present invention may include 1) obtaining an $I_{peak\ in\ parallel\ direction}/I_{peak\ in\ perpendicular\ direction}$ value of an electrode active material, on which a density is to be measured, by X-ray diffraction; and 2) calculating a targeted electrode density according to a correlation between the electrode density and the $I_{peak\ in\ parallel\ direction}/I_{peak\ in\ perpendicular\ direction}$ value of the electrode active material which are obtained in advance.

Also, a method of measuring an electrode porosity according to an embodiment of the present invention may include 1) obtaining an $I_{peak\ in\ parallel\ direction}/I_{peak\ in\ perpendicular\ direction}$ value of an electrode active material, on which a porosity is to be measured, by X-ray diffraction; and 2) calculating a targeted electrode porosity according to a correlation between the electrode porosity and the $I_{peak\ in\ parallel\ direction}/I_{peak\ in\ perpendicular\ direction}$ value of the electrode active material which are obtained in advance.

Since the methods of measuring electrode density and electrode porosity of the present invention use X-ray diffraction, there is no need to destruct a portion of the electrode for each measurement. Thus, the electrode density and electrode porosity may be measured simply and efficiently in terms of effort and time as well as cost.

The methods of measuring electrode density and electrode porosity according to the embodiments of the present invention will be described in detail with reference to the accompanying drawings.

Figure 1A:
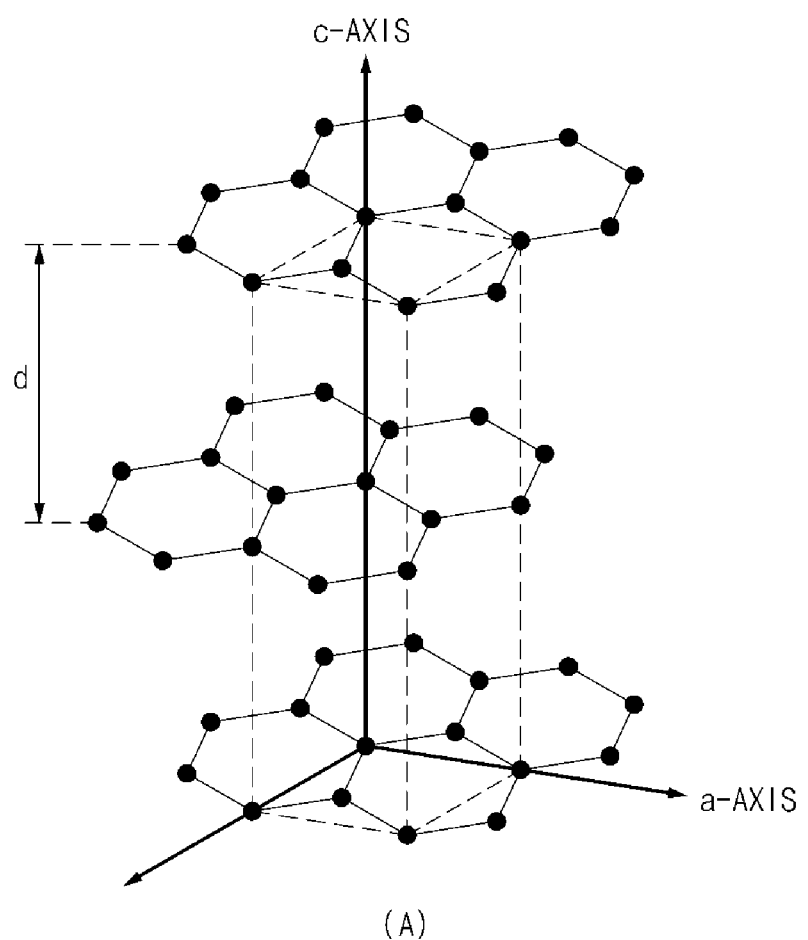
FIG. 1a illustrates a structure of an electrode active material coated on an electrode.
Figure 1B:
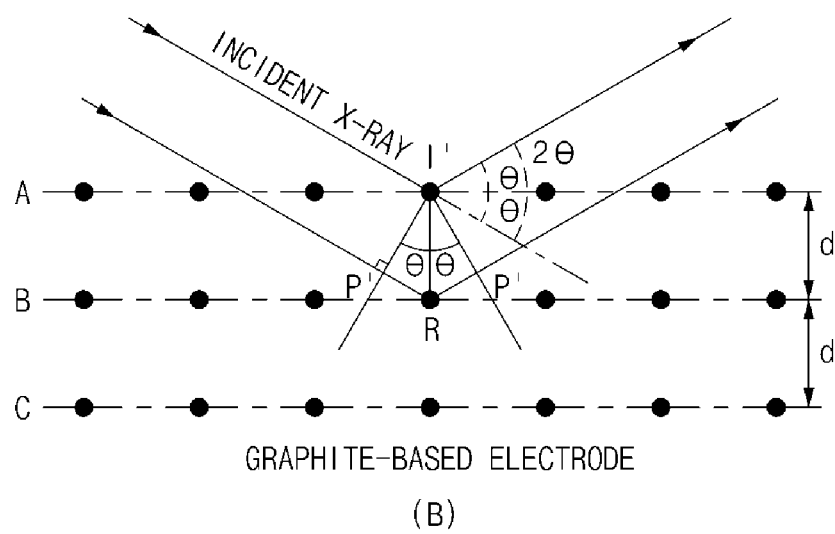
FIG. 1b illustrates the principle of X-ray diffraction.
Figure 1C:
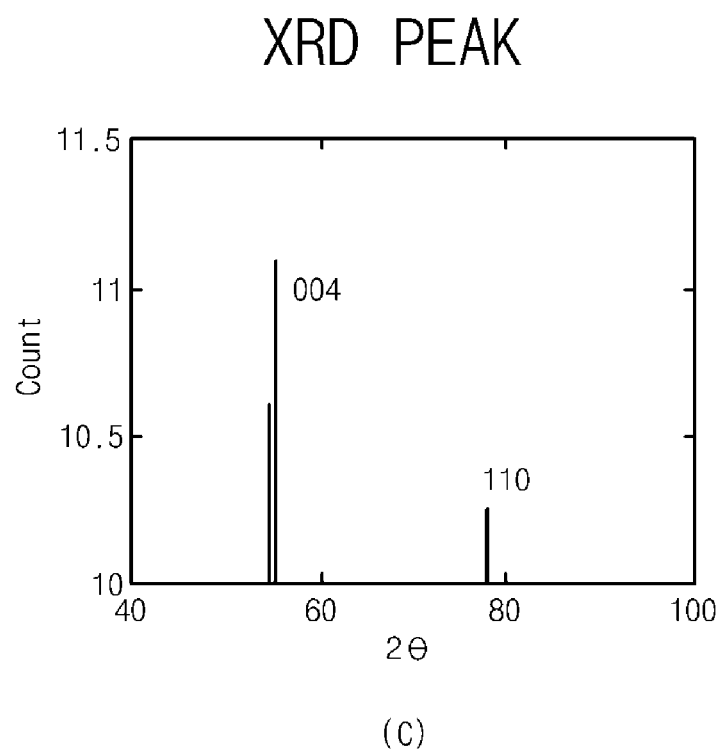
FIG. 1c is a graph illustrating peaks of the electrode active material (e.g., graphite) coated on the electrode which are obtained by X-ray diffraction.

FIG. 1 (FIGS. 1a to 1c) illustrates an X-ray diffraction measurement method of an electrode according to an embodiment of the present invention.

Referring to FIG. 1, FIG. 1a illustrates a structure of an electrode active material coated on an electrode, FIG. 1b illustrates the principle of X-ray diffraction, and FIG. 1c illustrates peaks of the electrode active material coated on the electrode which are obtained by X-ray diffraction.

According to an embodiment of the present invention, the electrode coated with the electrode active material as in FIG. 1 is irradiate with X-ray to obtain relative intensities of diffraction peaks according to an incident angle, and electrode density and electrode porosity may be measured using the relative intensities.

According to an embodiment of the present invention, the electrode active material may include a carbon-based active material.

Specifically, as in FIG. 1a, a structure of the electrode active material coated on the electrode, for example, graphite particles, is a hexagonal crystal structure with lattice parameters of a=2.46 Å and c=6.73 Å.

The electrode coated with graphite having the above crystal structure may be irradiated with X-ray as illustrated in FIG. 1b, and the principle thereof is as follows. That is, in a case where atoms in the graphite coated on the electrode are arranged on parallel lattice planes A, B, and C having spacing d, X-ray is scattered in all directions by the atoms when the X-ray with wavelength λ is incident on the crystal at incident angle θ. If P'RP" of the scattered X-ray is an integer multiple of the wavelength of the incident X-ray, the X-ray is intensified due to interference effects, and this phenomenon is referred to as a diffraction phenomenon. In a case where the diffraction phenomenon occurs, the following relationship between the wavelength λ of the incident X-ray, the incident angle θ, and the lattice spacing d is established. The relationship is known as the Bragg equation and is expressed by Equation 1 below:

$$d = \lambda/2 \sin \theta \qquad \text{<Equation 1>}$$

Also, FIG. 1c illustrates peaks obtained by X-ray diffraction as in FIG. 1b, wherein a plurality of diffraction peaks having different intensities are presented when X-ray diffraction intensities are recorded while continuously changing the angle of X-ray incident on the electrode coated with a graphite-based electrode active material, and for example, 004 peak and 110 peak may be obtained.

Specifically, according to an embodiment of the present invention, type and intensity of peaks of the electrode active material coated on the electrode obtained by X-ray diffraction may be different according to its orientation, and an example thereof is illustrated in FIG. 2.

Figure 2A:
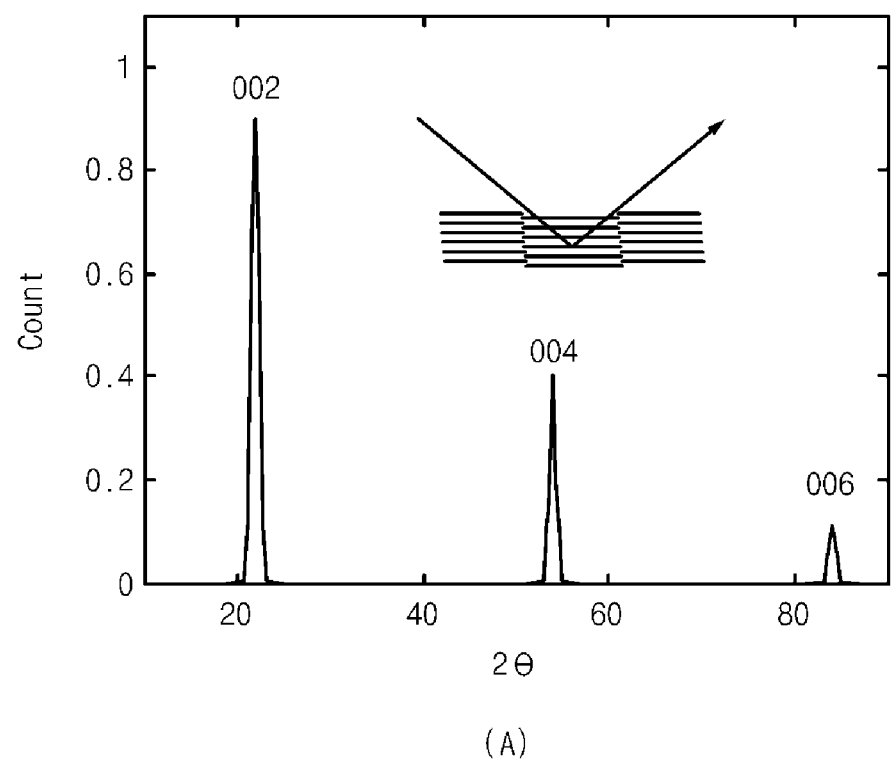
FIG. 2a is a graph illustrating peaks obtained by X-ray diffraction when an electrode active material is arranged parallel to a base plane of an electrode according to an embodiment of the present invention.

For example, if all carbon ring planes in the graphite-based active material are arranged parallel to a base plane of the electrode as illustrated in FIG. 2a, diffraction peaks, such as 002, 004, and 006 peaks, may only be observed.

Figure 2B:
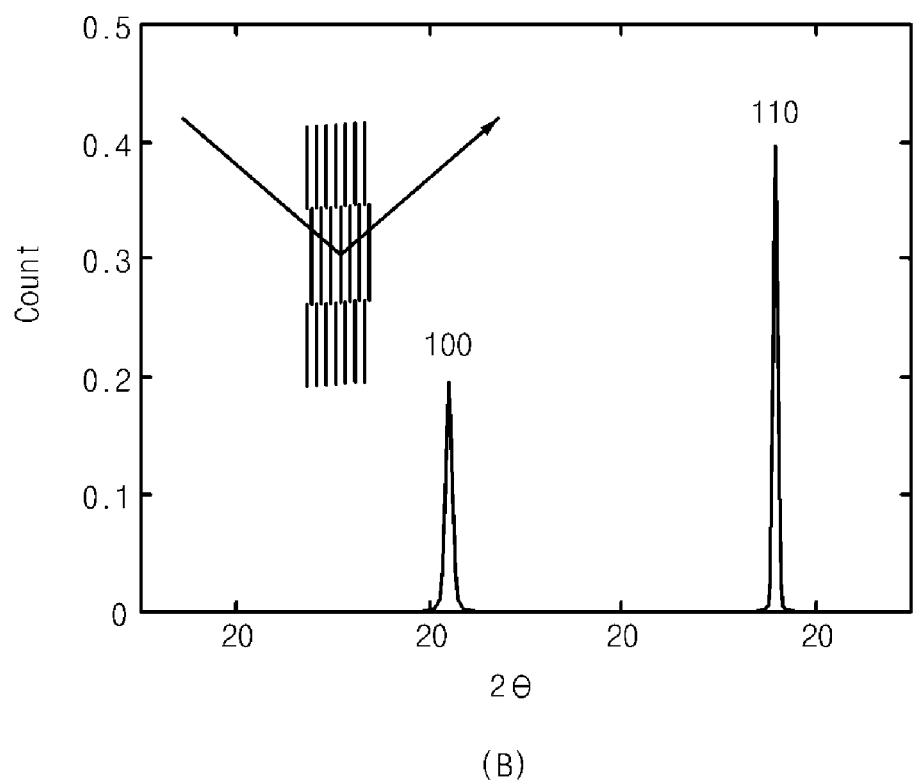
FIG. 2b is a graph illustrating peaks obtained by X-ray diffraction when an electrode active material is arranged perpendicular to the base plane of the electrode.

In contrast, if all carbon ring planes in the graphite-based active material are arranged perpendicular to the base plane of the electrode as illustrated in FIG. 2b, diffraction peaks, such as 100 and 110 peaks, may only be observed.

In general, an electrode density or electrode porosity of electrodes used in a lithium secondary battery is obtained by coating an electrode base material with a slurry including an electrode active material, drying a solvent, and pressing the dried electrode based material at an appropriate pressure. In this case, the electrode density is increased while the porosity decreases as the applied pressure increases.

According to an embodiment of the present invention, for example, with respect to an electrode coated with a graphite-based electrode active material, a ratio, in which an orientation of carbon ring planes is perpendicular to a base plane (see FIG. 2b), is decreased and a ratio, in which the orientation of the carbon ring planes is parallel to the base plane (see FIG. 2a), is increased as the pressure applied to the electrode increases.

Thus, the electrode density is in a high correlation with a value obtained by dividing an area ($I_{peak\ in\ parallel\ direction}$) of the peak in a parallel direction of the electrode active material illustrated in FIG. 2a that is arranged parallel to the base plane of the electrode by an area ($I_{peak\ in\ perpendicular\ direction}$) of the peak in a perpendicular direction of the electrode active material illustrated in FIG. 2b that is arranged perpendicular to the base plane of the electrode, i.e., $I_{peak\ in\ parallel\ direction}/I_{peak\ in\ perpendicular\ direction}$. Since the smaller the $I_{peak\ in\ parallel\ direction}/I_{peak\ in\ perpendicular\ direction}$ is the lower the electrode density is and the larger the $I_{peak\ in\ parallel\ direction}/I_{peak\ in\ perpendicular\ direction}$ is the higher the electrode density is, the correlation between the electrode density and the $I_{peak\ in\ parallel\ direction}/I_{peak\ in\ perpendicular\ direction}$ of the electrode active material may be a linear relationship with a high coefficient of determination.

The electrode porosity is in a high correlation with a value obtained by dividing an area ($I_{peak\ in\ parallel\ direction}$) of the peak in a parallel direction of the electrode active material illustrated in FIG. 2a that is arranged parallel to the base plane of the electrode by an area ($I_{peak\ in\ perpendicular\ direction}$) of the peak in a perpendicular direction of the electrode active material illustrated in FIG. 2b that is arranged perpendicular to the base plane of the electrode, i.e., $I_{peak\ in\ parallel\ direction}/I_{peak\ in\ perpendicular\ direction}$. Since the smaller the $I_{peak\ in\ parallel\ direction}/I_{peak\ in\ perpendicular\ direction}$ is the higher the electrode porosity is and the larger the $I_{peak\ in\ parallel\ direction}/I_{peak\ in\ perpendicular\ direction}$ is the lower the electrode porosity is, the correlation between the electrode porosity and the $I_{peak\ in\ parallel\ direction}/I_{peak\ in\ perpendicular\ direction}$ of the electrode active material may be a linear relationship with a high coefficient of determination.

The expression "coefficient of determination" used in the present invention denotes a coefficient of measuring whether a regression line estimated by sample observation explains an actually observed sample to some extent, that is, whether the regression line represents an actual observed value to some extent to show the goodness of fit, and may be defined as a value representing a correlation between X value and Y value. The coefficient of determination is represented as $R^2$ and is the same as the square of a correlation coefficient (R). $R^2$ is a value between 0 and 1, wherein the larger the $R^2$ value is, the higher the correlation is. When $R^2=1$, it denotes that all sample observations are on the estimated regression line. Thus, it denotes that the estimated regression line fully explains the relationship between variables.

Also, the expression "correlation coefficient" used in the present invention may be a statistical quantity for measuring the degree of a linear relationship between two variables, and may be defined as a numerical measure for measuring the strength of a linear relationship indicating how close points are scattered around a straight line.

The correlation coefficient is represented as "R", and R always has a value between −1 and 1. In this case, when R>0, x and y may be in a positive correlation, and this is a case in which when one variable increases, the other variable tends to increase. Also, when R<0, x and y may be in a negative correlation, and this is a case in which when one variable increases, the other variable tends to decrease. When R=0, x and y may be uncorrelated.

Also, the larger the absolute value of R is, the higher the linear relationship between x and y may be. When R is +1 or −1, it is a case in which all measured values are perfectly located on the straight line.

According to an embodiment of the present invention, electrode density and electrode porosity may be measured by the above-described principle.

First, in the method of measuring an electrode density according to the embodiment of the present invention, step 1) is obtaining an $I_{peak\ in\ parallel\ direction}/I_{peak\ in\ perpendicular\ direction}$ value of an electrode active material using X-ray diffraction of an electrode including the electrode active material, which is to be measured.

That is, an area ($I_{peak\ in\ parallel\ direction}$) of a peak in a parallel direction of an electrode active material that is arranged parallel to the base plane of the electrode and an area ($I_{peak\ in\ perpendicular\ direction}$) of a peak in a perpendicular direction of the electrode active material that is arranged perpendicular to the base plane of the electrode are obtained using X-ray diffraction of each electrode, and thus, a value obtained by dividing $I_{peak\ in\ parallel\ direction}$ by $I_{peak\ in\ perpendicular\ direction}$, i.e., $I_{peak\ in\ parallel\ direction}/I_{peak\ in\ perpendicular\ direction}$, may be obtained.

In the method of measuring an electrode density according to the embodiment of the present invention, step 2) may include calculating a targeted electrode density according to a previously obtained correlation between the electrode density and the $I_{peak\ in\ parallel\ direction}/I_{peak\ in\ perpendicular\ direction}$ value of the electrode active material which are obtained in advance.

The correlation between the electrode density and the $I_{peak\ in\ parallel\ direction}/I_{peak\ in\ perpendicular\ direction}$ value of the electrode active material, which are obtained in advance in step 2), may be obtained in such a manner that (a) densities of at least 3 or more electrodes including the same electrode active material are obtained according to a typical method, (b) an $I_{peak\ in\ parallel\ direction}/I_{peak\ in\ perpendicular\ direction}$ value of the electrode active material of the corresponding electrode is obtained using X-ray diffraction, and the correlation between the electrode density and the $I_{peak\ in\ parallel\ direction}/I_{peak\ in\ perpendicular\ direction}$ value is analyzed using the data obtained from (a) and (b).

Also, in the method of measuring an electrode porosity according to the embodiment of the present invention, step 1) is obtaining an $I_{peak\ in\ parallel\ direction}/I_{peak\ in\ perpendicular\ direction}$ value of an electrode active material using X-ray diffraction of an electrode including the electrode active material, which is to be measured. The $I_{peak\ in\ parallel\ direction}/I_{peak\ in\ perpendicular\ direction}$ value of the electrode active material may be obtained in the same manner as in step 1).

In the method of measuring an electrode porosity according to the embodiment of the present invention, step 2) may include calculating a targeted electrode porosity according to a previously obtained correlation between the electrode porosity and the value of $I_{peak\ in\ parallel\ direction}/I_{peak\ in\ perpendicular\ direction}$ of the electrode active material which are obtained in advance.

The correlation between the electrode porosity and the $I_{peak\ in\ parallel\ direction}/I_{peak\ in\ perpendicular\ direction}$ value of the electrode active material, which are obtained in advance in step 2), may be obtained in such a manner that (a) porosities of at least 3 or more electrodes including the same electrode active material are obtained according to a typical method, (b) an $I_{peak\ in\ parallel\ direction}/I_{peak\ in\ perpendicular\ direction}$ value of the electrode active material of the corresponding electrode is obtained using X-ray diffraction, and the correlation between the electrode porosity and the $I_{peak\ in\ parallel\ direction}/I_{peak\ in\ perpendicular\ direction}$ value is analyzed using the data obtained from (a) and (b).

According to an embodiment of the present invention, the $I_{peak\ in\ parallel\ direction}/I_{peak\ in\ perpendicular\ direction}$ may be $I_{002}/I_{100}$, $I_{002}/I_{110}$, $I_{004}/I_{100}$, $I_{004}/I_{110}$, $I_{006}/I_{100}$, or $I_{006}/I_{110}$.

A method typically used in the art may be used as the typical method of measuring electrode density (D) and electrode porosity (P), but the present invention is not limited thereto. For example, the electrode density (D) for obtaining the correlation may be calculated from the following Equation 2, and the electrode porosity (P) may be calculated from the following Equation 3.

$$D = M/(S \times H)$$ <Equation 2> where,

D represents an electrode density,

S is an electrode area,

M is a mass of an electrode active material excluding an electrode base material in an electrode, and H represents a thickness of the electrode active material excluding the electrode base material in the electrode.

$$P=[1-(D/T)]\times 100 \qquad \text{Equation 3>}$$

where,

P represents an electrode porosity,

D represents an electrode density, and

T represents a true density of an electrode active material excluding an electrode base material in an electrode.

Herein, the true density denotes an inherent density of an electrode active material without pores.

According to the methods of measuring electrode density and electrode porosity according to the embodiments of the present invention, if the correlation between the electrode density and the $I_{peak\ in\ parallel\ direction}/I_{peak\ in\ perpendicular\ direction}$ value of the electrode active material, and the correlation between the electrode porosity and the $I_{peak\ in\ parallel\ direction}/I_{peak\ in\ perpendicular\ direction}$ value of the electrode active material, which are calculated from Equations 2 and 3, are obtained in advance and stored, there is no need to destruct a portion of the electrode for each measurement when a targeted electrode active material is the same as the electrode active material used in the correlations. Thus, electrode density and electrode porosity may be efficiently and simply measured using X-ray diffraction.

According to an embodiment of the present invention, the electrode base material and the electrode active material used in the electrode may be a cathode base material, an anode base material, a cathode active material, or an anode active material, which are typically used in the art.

Specifically, non-limiting examples of the cathode base material may be aluminum, nickel, or a foil prepared by a combination thereof, and non-limiting examples of the anode base material may be copper, gold, nickel, or a copper alloy, or a foil prepared by a combination thereof.

The cathode active material may include a manganese-based spinel active material, lithium metal oxide, or a mixture thereof. Furthermore, the lithium metal oxide may be selected from the group consisting of lithium-cobalt-based oxide, lithium-manganese-based oxide, lithium-nickel-manganese-based oxide, lithium-manganese-cobalt-based oxide, and lithium-nickel-manganese-cobalt-based oxide, and for example, may include $LiCoO_2$, $LiNiO_2$, $LiMnO_2$, $LiMn_2O_4$, $Li(Ni_aCo_bMn_c)O_2$ (where $0<a<1$, $0<b<1$, $0<c<1$, and $a+b+c=1$), $LiNi_{1-y}Co_yO_2$, $LiCo_{1-y}Mn_yO_2$, $LiNi_{1-y}Mn_yO_2$ (where $0\leq Y<1$), $Li(Ni_aCo_bMn_c)O_4$ (where $0<a<2$, $0<b<2$, $0<c<2$, and $a+b+c=2$), $LiMn_{2-z}Ni_zO_4$, and $LiMn_{2-z}Co_zO_4$ (where $0<z<2$).

As the anode active material, a carbon-based anode active material, such as crystalline carbon, amorphous carbon, or a carbon composite, may be used alone or in combination of two or more thereof. Graphite-based carbon, such as natural graphite and artificial graphite, may be used as the crystalline carbon. According to an embodiment of the present invention, graphite as a carbon-based active material is described in detail as an example. However, the present invention is not limited thereto, and both cathode and anode active materials typically used in the art may be variously used.

According to an embodiment of the present invention, a coefficient of determination ($R^2$) of the electrode density obtained from the correlation is in a range of 0.6 to 1.0, may be in a range of 0.8 to 1.0, and for example, may be in a range of 0.9 to 1.0.

Also, according to an embodiment of the present invention, a coefficient of determination ($R^2$) of the electrode porosity obtained from the correlation is in a range of 0.6 to 1.0, may be in a range of 0.8 to 1.0, and for example, may be in a range of 0.9 to 1.0. When the coefficients of determination ($R^2$) of the electrode density and the electrode porosity are outside the above range, error ranges of the targeted electrode density and the electrode porosity may be increased, and thus, reliability may decrease.

As described above, electrode density and electrode porosity may be efficiently measured by a non-destructive method using X-ray diffraction according to the embodiments of the present invention, and values of the electrode density and electrode porosity obtained by the above methods have considerably high accuracy.

Hereinafter, the present invention will be described in detail, according to specific examples. The invention may, however, be embodied in many different forms and should not be construed as being limited to the embodiments set forth herein. Rather, these example embodiments are provided so that this description will be thorough and complete, and will fully convey the scope of the present inventive concept to those skilled in the art.

EXAMPLES

Hereinafter, the present invention will be described in more detail, according to examples and experimental examples. However, the present invention is not limited thereto.

Anode Preparation

Preparation Example 1

An anode mixture slurry was prepare by adding 96 wt % of graphite as an anode active material, 1 wt % of carboxymethyl cellulose (CMC) and 2 wt % of a styrene-butadiene rubber (SBR) as a binder, and 1 wt % of carbon black as a conductive agent to water as a solvent. An about 21.2 μm thick copper (Cu) thin film, as an anode base material, was coated with the anode mixture slurry and dried. Then, an anode having a thickness of 61.8 μm was prepared by roll-pressing the dried anode coated with the anode mixture slurry.

Preparation Example 2

An anode was prepared in the same manner as in Preparation Example 1 except that a thickness of the anode was 54.2 μm.

Preparation Example 3

An anode was prepared in the same manner as in Preparation Example 1 except that a thickness of the anode was 49.8 μm.

Preparation Example 4

An anode was prepared in the same manner as in Preparation Example 1 except that a thickness of the anode was 49.1 μm.

Preparation Example 5

An anode was prepared in the same manner as in Preparation Example 1 except that a thickness of the anode was 47.0 μm.

Preparation Example 6

An anode was prepared in the same manner as in Preparation Example 1 except that a thickness of the anode was 52.0 μm.

Preparation Example 7

An anode was prepared in the same manner as in Preparation Example 1 except that a thickness of the anode was 48.5 μm.

Example 1

<Density Measurement of Anode>

1) Obtain Correlation Between Anode Density and $I_{004}/I_{110}$ of Anode Active Material Specific areas were sampled from the anodes prepared in Preparation Examples 1 to 5 to measure areas, masses, and thicknesses of the sampled anodes, and the result was substituted into Equation 2 to obtain anode densities (D). The results thereof are presented in Table 1 below:

TABLE 1

| | Anode Area (S), cm$^2$ | Anode mass-copper mass (M), mg | Anode thickness, μm | Anode thickness-copper thickness (H), μm | Anode density (D)M/(S × H), g/cm$^3$ |
|---|---|---|---|---|---|
| Preparation Example 1 | 1.4875 | 6.06 | 61.8 | 40.6 | 1.00 |
| Preparation Example 2 | 1.4875 | 6.07 | 54.2 | 33.0 | 1.24 |
| Preparation Example 3 | 1.4875 | 6.05 | 49.8 | 28.6 | 1.42 |
| Preparation Example 4 | 1.4875 | 6.02 | 49.1 | 27.9 | 1.45 |
| Preparation Example 5 | 1.4875 | 6.05 | 47.0 | 25.8 | 1.58 |

The areas of the sampled anodes were the same for all samples, namely 1.4875 cm$^2$, and the anode thickness included the thickness (21.2 μm) of copper.

$I_{004}/I_{110}$ of the anode active materials were obtained from the anodes prepared in Preparation Examples 1 to 5 by X-ray diffraction, and the results thereof are presented in Table 2 below:

TABLE 2

| | $I_{004}$ | $I_{110}$ | $I_{004}/I_{110}$ |
|---|---|---|---|
| Preparation Example 1 | 2541 | 94.30 | 26.95 |
| Preparation Example 2 | 3195 | 73.78 | 43.31 |
| Preparation Example 3 | 4105 | 74.82 | 54.87 |
| Preparation Example 4 | 3595 | 59.75 | 60.17 |
| Preparation Example 5 | 3738 | 52.20 | 71.61 |

Figure 3:
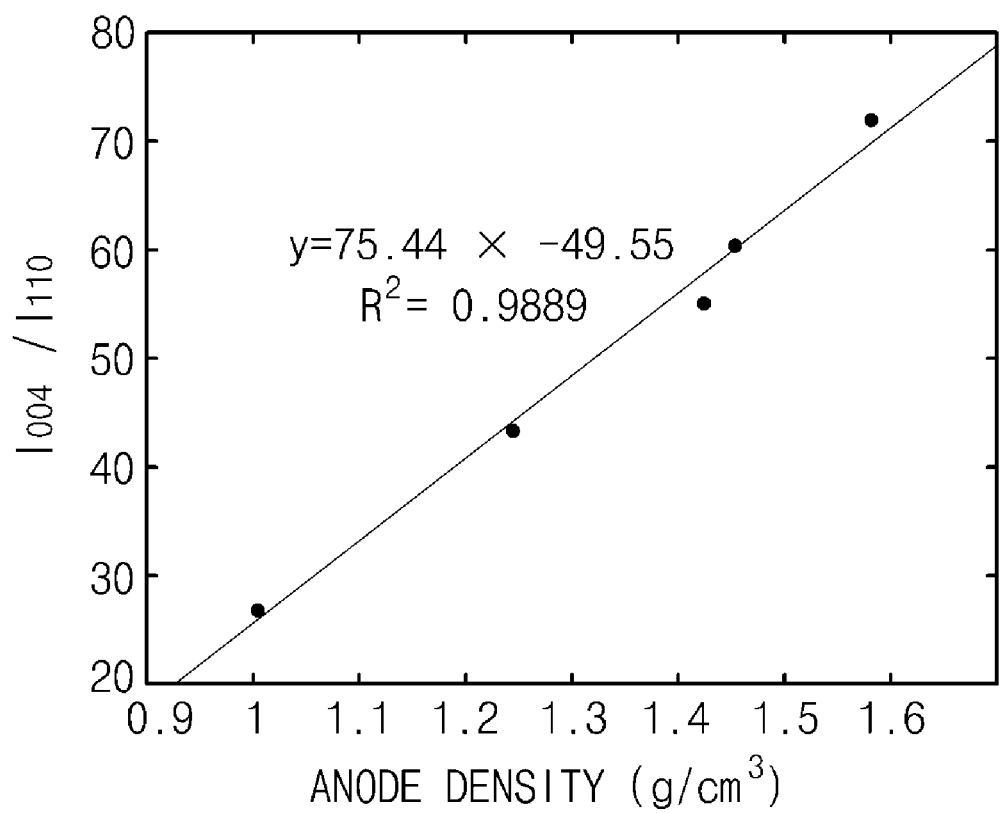
FIG. 3 is a graph illustrating a correlation between electrode density and $I_{004}/I_{110}$ according to an embodiment of the present invention.

A correlation was obtained using the anode densities and the $I_{004}/I_{110}$ of the anode active materials by X-ray diffraction presented in Tables 1 and 2, and the results thereof are illustrated in FIG. 3.

As illustrated in FIG. 3, the anode densities and the $I_{004}/I_{110}$ of the anode active materials obtained from the anodes prepared in Preparation Examples 1 to 5 exhibited a linear relationship with a high coefficient of determination ($R^2$). That is, referring to a correlation graph of the anode density and $I_{004}/I_{110}$ of FIG. 3, $R^2=0.9889$ and thus, it may be confirmed that $R^2$ was a value close to 1. This indicates that most of the measured density values of the anodes were located on a regression line and had a very high correlation.

2) Obtain $I_{004}/I_{110}$ Value of Anode Active Material, on which Density is to be Measured, Using X-Ray Diffraction Targeted $I_{004}/I_{110}$ values of the graphite active materials in the anodes prepared in Preparation Examples 6 and 7 are presented in Table 3 below.

TABLE 3

| | $I_{004}/I_{110}$ |
|---|---|
| Preparation Example 6 | 52.10 |
| Preparation Example 7 | 62.82 |

3) Calculating Anode Density

Densities of the anodes prepared in Preparation Examples 6 and 7 may be obtained by substituting the $I_{004}/I_{110}$ values of the graphite active materials obtained using X-ray diffraction in 2) into the correlation, i.e., the graph of FIG. 3, and the results thereof are presented in Table 4 below.

TABLE 4

| | Anode density (g/cm$^3$) |
|---|---|
| Preparation Example 6 | 1.35 |
| Preparation Example 7 | 1.49 |

Comparative Example 1: Measurement of Anode Densities of Preparation Examples 6 and 7 by Typical Method of Calculating Electrode Density (Equation 2)

Specific areas were sampled from the anodes prepared in Preparation Examples 6 and 7 to measure areas, masses, and thicknesses of the anodes, and anode densities (D) were obtained using the measured data. The results thereof are presented in Table 5 below.

TABLE 5

| | Anode Area (S), cm$^2$ | Anode mass-copper mass (M), mg | Anode thickness, μm | Anode thickness-copper thickness (H), μm | Anode density (D)M/(S × H), mg/cm$^3$ |
|---|---|---|---|---|---|
| Preparation Example 6 | 1.4875 | 6.11 | 52.0 | 30.8 | 1.33 |
| Preparation Example 7 | 1.4875 | 6.08 | 48.5 | 27.3 | 1.50 |

It may be understood that the anode densities obtained using X-ray diffraction in Table 4 and the anode density values obtained by sampling the specific areas of the anodes in Table 5 were very close to each other. Thus, it may be understood that the anode densities (g/cm³) calculated from the correlation were considerably accurate values.

Example 2

<Porosity Measurement of Anode>
1) Obtain Correlation Between Anode Porosity and $I_{004}/I_{110}$ of Anode Active Material Specific areas were sampled from the anodes prepared in Preparation Examples 1 to 5 to measure masses and thicknesses of the sampled anodes, and anode densities (D) were obtained using the measured data. True density (T, 2.11 g/cm³) of graphite was substituted into Equation 3 to measure anode porosities (P). The results thereof are presented in Table 6 below:

TABLE 6

|  | Anode density (D), g/cm³ | True density of graphite (T), g/cm³ | Anode porosity (P) [1-(D/T)] × 100, % |
|---|---|---|---|
| Preparation Example 1 | 1.00 | 2.11 | 52.4 |
| Preparation Example 2 | 1.24 | 2.11 | 41.3 |
| Preparation Example 3 | 1.42 | 2.11 | 32.5 |
| Preparation Example 4 | 1.45 | 2.11 | 31.3 |
| Preparation Example 5 | 1.58 | 2.11 | 25.2 |

A correlation was obtained using the anode porosities of Table 6 and the $I_{004}/I_{110}$ of the anode active materials by X-ray diffraction presented in Table 2 of Example 1.

Figure 4:
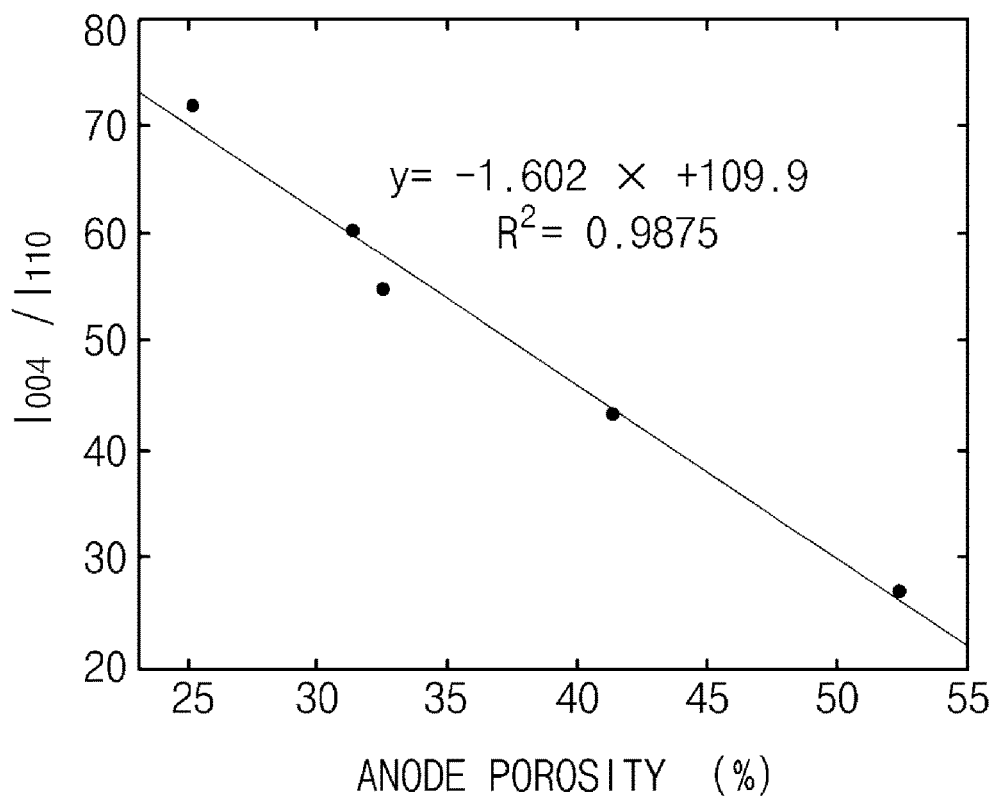
FIG. 4 is a graph illustrating a correlation between electrode porosity and $I_{004}/I_{110}$ according to an embodiment of the present invention.

As illustrated in FIG. 4, the anode porosities and the $I_{004}/I_{110}$ of the anode active materials obtained from the anodes prepared in Preparation Examples 1 to 5 exhibited a linear relationship with a high coefficient of determination. That is, referring to a correlation graph of the anode porosity and $I_{004}/I_{110}$ of FIG. 4, $R^2$=0.9875 and thus, it may be confirmed that $R^2$ was a value close to 1. This indicates that most of the measured porosity values of the anodes were located on a regression line and had a very high correlation.

2) Obtain $I_{004}/I_{110}$ Value of Anode Active Material, on which Porosity is to be Measured, Using X-Ray Diffraction The values presented in Table 3 of Example 1 were used as $I_{004}/I_{110}$ values of the graphite active materials in the anodes prepared in Preparation Examples 6 and 7.

3) Calculating Anode Porosity

Porosities (%) of the anodes prepared in Preparation Examples 6 and 7 may be obtained by substituting the $I_{004}/I_{110}$ values of the graphite active materials obtained using X-ray diffraction in 2) into the graph of FIG. 4, and the results thereof are presented in Table 7 below.

TABLE 7

|  | Anode porosity (%) |
|---|---|
| Preparation Example 6 | 36.1 |
| Preparation Example 7 | 29.4 |

Comparative Example 2: Measurement of Anode Porosities of Preparation Examples 6 and 7 by Typical Method of Calculating Electrode Porosity (Equation 3)

Specific areas were sampled from the anodes prepared in Preparation Examples 6 and 7 to measure areas, masses, and thicknesses of the anodes, and anode densities (D) were obtained as in Table 5. Anode porosities (P) were calculated using the above data as in Table 8.

TABLE 8

|  | Anode density (D), g/cm³ | True density of graphite (T), g/cm³ | Anode porosity (P) ((1-D)/T × 100), % |
|---|---|---|---|
| Preparation Example 6 | 1.33 | 2.11 | 36.7 |
| Preparation Example 7 | 1.50 | 2.11 | 29.0 |

It may be understood that the anode porosities obtained using X-ray diffraction in Table 7 and the anode porosity values obtained by sampling the specific areas of the anodes in Table 8 were very close to each other. Thus, it may be understood that the anode porosities (%) calculated from the correlation were considerably accurate values.

INDUSTRIAL APPLICABILITY

According to methods of measuring electrode density and porosity of the present invention, electrode density and porosity may be efficiently measured by a non-destructive method using X-ray diffraction while reducing errors.

The invention claimed is:

1. A method of non-destructively measuring an electrode density of an electrode active material coated on an electrode base material, the method comprising:

obtaining non-destructively an $I_{peak\ in\ parallel\ direction}/I_{peak\ in\ perpendicular\ direction}$ value of an electrode active material coated on an electrode base material by X-ray diffraction; and calculating an electrode density according to a previously obtained correlation between the electrode density and the $I_{peak\ in\ parallel\ direction}/I_{peak\ in\ perpendicular\ direction}$ value of the same type of electrode active material, wherein the electrode active material is a crystalline material, wherein $I_{peak\ in\ parallel\ direction}$ is an intensity peak when the crystal planes for the electrode active material are arranged parallel to a base plane of the electrode, wherein $I_{peak\ in\ perpendicular\ direction}$ is an intensity peak when the crystal planes for the electrode active material are arranged perpendicular to a base plane of the electrode, wherein the correlation between the electrode density and the $I_{peak\ in\ parallel\ direction}/I_{peak\ in\ perpendicular\ direction}$ value is obtained in advance by obtaining electrode densities of at least three or more electrodes including a same electrode active material according to Equation 2, measuring an $I_{peak\ in\ parallel\ direction}/I_{peak\ in\ perpendicular\ direction}$ value of the electrode active material of the corresponding electrode by X-ray diffraction, and analyzing a correlation between the three or more values of electrode density according to Equation 2 and $I_{peak\ in\ parallel\ direction}/I_{peak\ in\ perpendicular\ direction}$ value of the electrode active material:

$$D=M/(S\times H) \qquad <\text{Equation 2}>,$$

where D represents an electrode density, S is an electrode area, M is a mass of an electrode active material excluding an electrode base material in an electrode, and H represents a thickness of the electrode active material excluding the electrode base material in the electrode.

2. The method of claim 1, wherein the electrode active material comprises a crystalline carbon-based active material.

3. The method of claim 1, wherein the $I_{peak\ in\ parallel\ direction}/I_{peak\ in\ perpendicular\ direction}$ of the electrode active material is $I_{002}/I_{100}$, $I_{002}/I_{110}$, $I_{004}/I_{100}$, $I_{004}/I_{110}$, $I_{006}/I_{100}$, or $I_{006}/I_{110}$.

4. The method of claim 1, wherein in the correlation, the electrode density and the $I_{peak\ in\ parallel\ direction}/I_{peak\ in\ perpendicular\ direction}$ of the electrode active material have a linear relationship.

5. The method of claim 4, wherein in the correlation, a coefficient of determination ($R^2$) of the electrode density is in a range of 0.6 to 1.0.

6. A method of non-destructively measuring an electrode porosity of an electrode active material coated on an electrode base material, the method comprising:

obtaining non-destructively an $I_{peak\ in\ parallel\ direction}/I_{peak\ in\ perpendicular\ direction}$ value of an electrode active material coated on an electrode base material by X-ray diffraction; and calculating an electrode porosity according to a previously obtained correlation between the electrode porosity and the $I_{peak\ in\ parallel\ direction}/I_{peak\ in\ perpendicular\ direction}$ value of the same type of electrode active material, wherein the electrode active material is a crystalline material, wherein $I_{peak\ in\ parallel\ direction}$ is an intensity peak when the crystal planes for the electrode active material are arranged parallel to a base plane of the electrode, wherein $I_{peak\ in\ perpendicular\ direction}$ is an intensity peak when the crystal planes for the electrode active material are arranged perpendicular to a base plane of the electrode, wherein the correlation between the electrode porosity and $I_{peak\ in\ parallel\ direction}/I_{peak\ in\ perpendicular\ direction}$ value of the electrode active material is obtained in advance by obtaining electrode porosities of at least three or more electrodes including a same electrode active material according to Equation 3 and measuring an $I_{peak\ in\ parallel\ direction}/I_{peak\ in\ perpendicular\ direction}$ value of the electrode active material of the corresponding electrode by X-ray diffraction, and analyzing a correlation between the electrode porosity obtained according to Equation 3 and the $I_{peak\ in\ parallel\ direction}/I_{peak\ in\ perpendicular\ direction}$ value of the electrode active material:

$$P=[1-(D/T)]\times 100 \qquad <\text{Equation 3}>,$$

where P represents an electrode porosity, D represents an electrode density, and T represents a true density of an electrode active material excluding an electrode base material in an electrode.

7. The method of claim 6, wherein the electrode active material comprises a crystalline carbon-based active material.

8. The method of claim 6, wherein the $I_{peak\ in\ parallel\ direction}/I_{peak\ in\ perpendicular\ direction}$ of the electrode active material is $I_{002}/I_{100}$, $I_{002}/I_{110}$, $I_{004}/I_{100}$, $I_{004}/I_{110}$, $I_{006}/I_{100}$, or $I_{006}/I_{110}$.

9. The method of claim 6, wherein in the correlation, the electrode porosity and the $I_{peak\ in\ parallel\ direction}/I_{peak\ in\ perpendicular\ direction}$ of the electrode active material have a linear relationship.

10. The method of claim 6, wherein in the correlation, a coefficient of determination ($R^2$) of the electrode porosity is in a range of 0.6 to 1.0.

* * * * *